United States Patent
Kobayashi

(10) Patent No.: US 9,061,332 B2
(45) Date of Patent: Jun. 23, 2015

(54) TREATMENT SYSTEM OF WET ORGANIC WASTE

(75) Inventor: Takaitsu Kobayashi, Chiba (JP)

(73) Assignee: URAYASU DENSETSU K.K., Chiba (JP)

( * ) Notice: Subject to any disclaimer, the term of this patent is extended or adjusted under 35 U.S.C. 154(b) by 421 days.

(21) Appl. No.: 13/501,536

(22) PCT Filed: Oct. 14, 2010

(86) PCT No.: PCT/JP2010/068016
§ 371 (c)(1),
(2), (4) Date: Apr. 12, 2012

(87) PCT Pub. No.: WO2011/046162
PCT Pub. Date: Apr. 21, 2011

(65) Prior Publication Data
US 2012/0202280 A1 Aug. 9, 2012

(30) Foreign Application Priority Data
Oct. 16, 2009 (JP) .................................. 2009-239069

(51) Int. Cl.
*C12M 1/00* (2006.01)
*C12M 3/00* (2006.01)
(Continued)

(52) U.S. Cl.
CPC ... *B09B 3/00* (2013.01); *C05F 7/00* (2013.01); *C12M 21/04* (2013.01); *C12M 47/14* (2013.01); *F23G 7/001* (2013.01); *F23G 2900/50208* (2013.01)

(58) Field of Classification Search
CPC ...... C12M 31/00; C12M 21/02; C12M 21/04; C12M 23/34; C12M 43/04; C12M 43/06
See application file for complete search history.

(56) References Cited

U.S. PATENT DOCUMENTS 5,659,977 A * 8/1997 Jensen et al. .................... 34/547
6,569,332 B2 * 5/2003 Ainsworth et al. ........... 210/603
(Continued)

FOREIGN PATENT DOCUMENTS

| JP | 52-61366 | 5/1977 |
| JP | 56-105725 | 8/1981 |

(Continued)

OTHER PUBLICATIONS

English translation of JP 2001-19578, Wakui et al, 2001.*
(Continued)

*Primary Examiner* — Nathan Bowers
(74) *Attorney, Agent, or Firm* — Wenderoth, Lind & Ponack, L.L.P.

(57) ABSTRACT

Provided is a treatment system whereby a wet organic waste can be effectively treated and $CO_2$ produced in the course of the treatment can be immobilized to thereby contribute to the reduction of $CO_2$. The treatment system is characterized by including microbiologically fermenting a wet organic waste in a fermentation device, combusting in a combustion furnace a fermented material obtained from the fermentation device and, at the same time, supplying to the combustion furnace a fermentation gas produced by the microbiological fermentation treatment in the fermentation device, and then recovering and immobilizing $CO_2$ in a hot exhaust gas produced by the combustion treatment in the combustion furnace.

6 Claims, 6 Drawing Sheets

(51) Int. Cl.
  *B09B 3/00* (2006.01)
  *C05F 7/00* (2006.01)
  *C12M 1/107* (2006.01)
  *F23G 7/00* (2006.01)

(56) References Cited

U.S. PATENT DOCUMENTS

| | | | |
|---|---|---|---|
| 2008/0009055 A1* | 1/2008 | Lewnard | 435/262 |
| 2008/0153145 A1* | 6/2008 | Harper | 435/165 |
| 2009/0227003 A1* | 9/2009 | Blotsky et al. | 435/257.1 |
| 2010/0105127 A1* | 4/2010 | Ginsburg | 435/262 |
| 2011/0003357 A1* | 1/2011 | Barclay et al. | 435/167 |
| 2011/0020862 A1* | 1/2011 | Audebert et al. | 435/41 |
| 2011/0039317 A1* | 2/2011 | Medoff | 435/155 |
| 2011/0070628 A1* | 3/2011 | Hornung et al. | 435/257.1 |
| 2011/0151547 A1* | 6/2011 | Bloch et al. | 435/262.5 |
| 2011/0165638 A1* | 7/2011 | Kotelko et al. | 435/134 |
| 2014/0011263 A1* | 1/2014 | Berzin | 435/257.1 |

FOREIGN PATENT DOCUMENTS

| | | |
|---|---|---|
| JP | 11-002402 | 1/1999 |
| JP | 2000-107731 | 4/2000 |
| JP | 2001-19578 | 1/2001 |
| JP | 2001-192287 | 7/2001 |
| JP | 2002-308685 | 10/2002 |
| JP | 2003-001228 | 1/2003 |
| JP | 2003-148186 | 5/2003 |
| JP | 2008-272535 | 11/2008 |

OTHER PUBLICATIONS

International Search Report issued Jan. 11, 2011 in International (PCT) Application No. PCT/JP2010/068016, of which the present application is the national stage.

* cited by examiner

TREATMENT SYSTEM OF WET ORGANIC WASTE

TECHNICAL FIELD

The present invention relates to a treatment system, which treats a wet organic waste such as a food residue and sewage sludge.

BACKGROUND ART

Recently, a treatment amount of the wet organic waste such as the food residue and the sewage sludge increases, and attention is focused on recycling of the wet organic waste by effectively treating the wet organic waste and using a product at the time of treatment as a resource.

For example, as disclosed in the following Patent Literatures 1 and 2, a device, which recycles the wet organic waste by performing microbial fermentation treatment of the wet organic waste in a fermentation device and using a fermented material obtained thereby as compost, and a method thereof are suggested.

CITATION LIST

Patent Literature

Patent Literature 1: Japanese Patent Application Laid-Open (JP-A) No. 2001-192287
Patent Literature 2: JP-A No. 2002-308685

SUMMARY OF INVENTION

Technical Problem

As described above, the Patent Literatures 1 and 2 relate to technology to perform the microbial fermentation treatment of the wet organic waste and use the fermented material obtained thereby as the compost.

On the other hand, although a large amount of fermentation gas such as ammonia gas and water vapor is produced together with air in the course of the microbial fermentation treatment (fermentation treatment by aerobic bacteria), the fermentation gas is conventionally subjected to combustion treatment to be deodorized and is discarded actually.

However, the combustion treatment produces a large amount of $CO_2$ and nitrogen oxide, and it is not possible to solve a problem to prevent global warming by reducing $CO_2$ and the like in atmosphere.

Solution to Problem

The present invention is to provide the treatment system, which effectively solves the problem of such conventional treatment system of the wet organic waste, thereby contributing to reduction in $CO_2$.

In summary, the microbial fermentation treatment of the wet organic waste is performed in the fermentation device, the combustion treatment of the fermented material obtained from the fermentation device is performed in a combustion furnace, and at the same time, the fermentation gas produced by the microbial fermentation treatment in the fermentation device is supplied to the combustion furnace, and $CO_2$ in hot exhaust gas produced by the combustion treatment in the combustion furnace is recovered to be immobilized such that $CO_2$ is not released again into the atmosphere.

Preferably, $CO_2$ in the hot exhaust gas is supplied to a plant growth facility to promote photonic synthesis of a plant, thereby immobilizing $CO_2$.

Further, the hot exhaust gas produced by the combustion treatment in the combustion furnace is subjected to wash treatment by a shower, and hot water obtained by contact between shower water and the hot exhaust gas is supplied to the plant growth facility to be used for heating the facility.

Preferably, heat exchange is performed between the fermentation gas produced by the microbial fermentation treatment in the fermentation device and the hot exhaust gas produced by the combustion treatment in the combustion furnace, and the fermentation gas heated by the heat exchange is supplied to the combustion furnace.

Further, combustion-supporting air is supplied to the fermentation device and the combustion-supporting air is recovered together with the fermentation gas produced by the microbial fermentation treatment to be supplied to the combustion furnace as combustion-supporting gas.

Further, as a preferable illustration, the fermentation device formed of a well-known kiln-type fermentation device includes a fermenting unit, which performs the microbial fermentation treatment, on a front half side of the inside of a cylindrical kiln of the kiln-type fermentation device, and a drying unit, which performs drying treatment of the fermented material subjected to the microbial fermentation treatment in the fermenting unit, on a rear half side of the inside thereof, and recovers the fermentation gas produced by the microbial fermentation treatment from the fermenting unit to supply to the combustion furnace.

Advantageous Effects of Invention

Therefore, according to the present invention, it is possible to perform the microbial fermentation treatment of the wet organic waste and perform the combustion treatment of the fermented material obtained thereby, and at the same time, perform the combustion treatment or heating treatment of the fermentation gas obtained by the microbial fermentation treatment in the combustion furnace, and immobilize $CO_2$ in the hot exhaust gas to contribute to the reduction in $CO_2$.

For example, as $CO_2$ immobilizing means, $CO_2$ in the hot exhaust gas produced in the combustion furnace is supplied to the plant growth facility to promote the photonic synthesis of the plant, thereby certainly immobilizing $CO_2$.

Further, the wash treatment of the hot exhaust gas produced in the combustion furnace is performed by the shower to remove combustion ash, and at the same time, the hot water obtained by the contact between the shower water and the hot exhaust gas is supplied to the plant growth facility for heating the facility, thereby realizing stable growth of the plant.

Further, it becomes possible to perform the heat exchange between the fermentation gas produced in the fermentation device and the hot exhaust gas produced in the combustion furnace and supply the fermentation gas heated by the heat exchange to the combustion furnace, thereby effectively performing the combustion treatment or the heating treatment of the fermentation gas.

Further, the combustion-supporting air is actively supplied to the fermentation device and the combustion-supporting air is recovered together with the fermentation gas produced by the microbial fermentation treatment to be supplied to the combustion furnace as the combustion-supporting gas to promote the combustion treatment of the fermented material in the combustion furnace.

Further, the fermenting unit, which performs the microbial fermentation treatment, is provided on the front half side of the inside of the cylindrical kiln of the fermentation device, and the drying unit, which performs the drying treatment of the fermented material subjected to the fermentation treatment in the fermenting unit, is provided on the rear half side of the inside thereof, and the fermentation gas produced by the microbial fermentation treatment is recovered from the fermenting unit and the fermentation gas including heat is efficiently recovered.

DESCRIPTION OF EMBODIMENTS

In the present invention, microbial fermentation treatment of a wet organic waste is performed in a fermentation device, combustion of a fermented material obtained from the fermentation device is performed in a combustion furnace, and at the same time, fermentation gas produced by the microbial fermentation treatment in the fermentation device is supplied to the combustion furnace, and $CO_2$ in hot exhaust gas produced by combustion treatment in the combustion furnace is recovered and immobilized such that $CO_2$ is not released again into atmosphere.

First Embodiment

Figure 1:
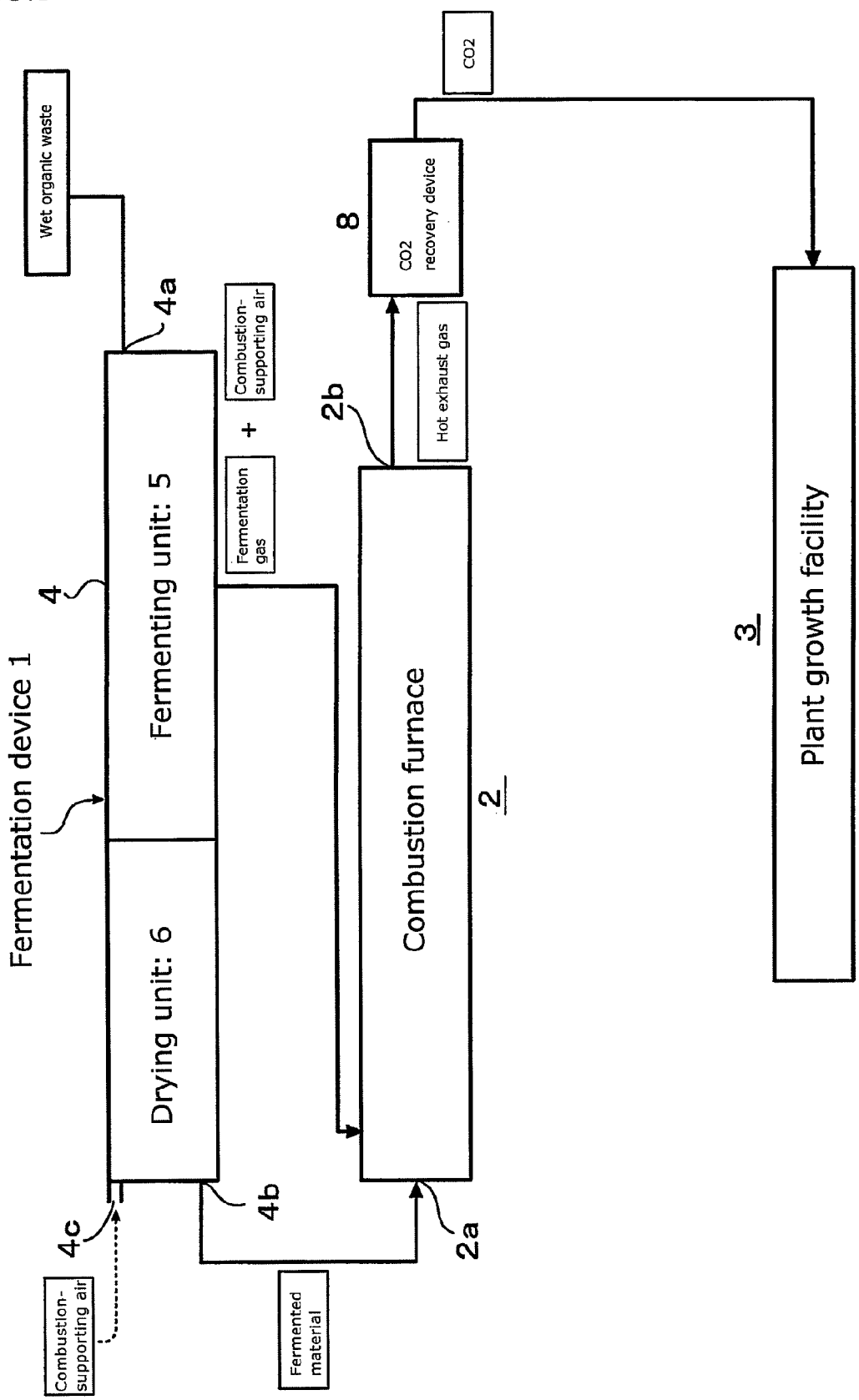
FIG. 1 is a flowchart schematically illustrating a treatment system of a wet organic waste according to a first embodiment of the present invention.

Hereinafter, the present invention is described in detail based on an illustrated preferred embodiment; as illustrated in FIG. 1, a treatment system of the wet organic waste according to a first embodiment is configured to perform the microbial fermentation treatment of the wet organic waste by aerobic bacteria in a fermentation device 1, perform the combustion treatment of the fermented material obtained from the fermentation device 1 in a combustion furnace 2, and at the same time, supply the fermentation gas produced by the microbial fermentation treatment in the fermentation device 1 to the combustion furnace 2 together with combustion-supporting air supplied to the fermentation device 1 as combustion-supporting gas, and recover $CO_2$ in the hot exhaust gas produced by the combustion treatment in the combustion furnace 2 to supply to a plant growth facility 3 to promote photonic synthesis of a plant, thereby immobilizing $CO_2$.

Herein, the fermentation gas is intended to mean gas including carbon dioxide, ammonia, water vapor and the like produced by the microbial fermentation treatment.

First, the fermentation device 1 is described in detail; as a preferred illustration, the fermentation device 1 formed of a well-known kiln-type fermentation device is provided with an input port 4a for the wet organic waste on a front end of a cylindrical kiln 4, an output port 4b through which the fermented material is taken out and a vent 4c through which the combustion-supporting air is delivered on a rear end thereof, a fermenting unit 5, which performs the microbial fermentation treatment, on a front half side of the inside thereof subsequent to the input port 4a, and a drying unit 6, which performs drying treatment of the fermented material subjected to the microbial fermentation treatment in the fermenting unit 5, on a rear half side of the inside thereof followed by the output port 4b and the vent 4c, and is configured to allow the combustion-supporting air heated in the drying unit 6 to flow to the fermenting unit 5, recover the fermented material through the output port 4b to supply to the combustion furnace 2, and at the same time, recover the fermentation gas produced in the fermenting unit 5 together with the combustion-supporting air to supply to the combustion furnace 2.

Figure 2:
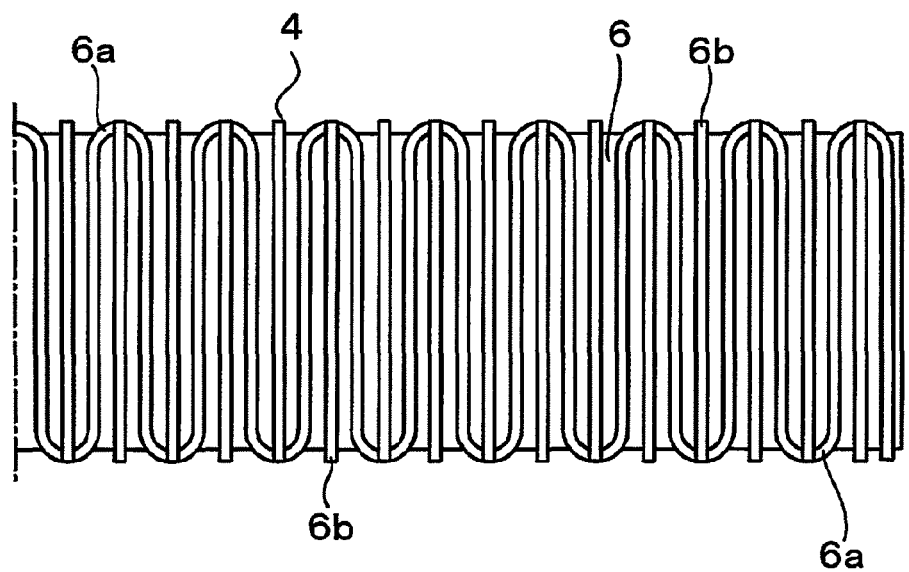
FIG. 2 is a bottom view of a drying unit of a fermentation device.
Figure 3:
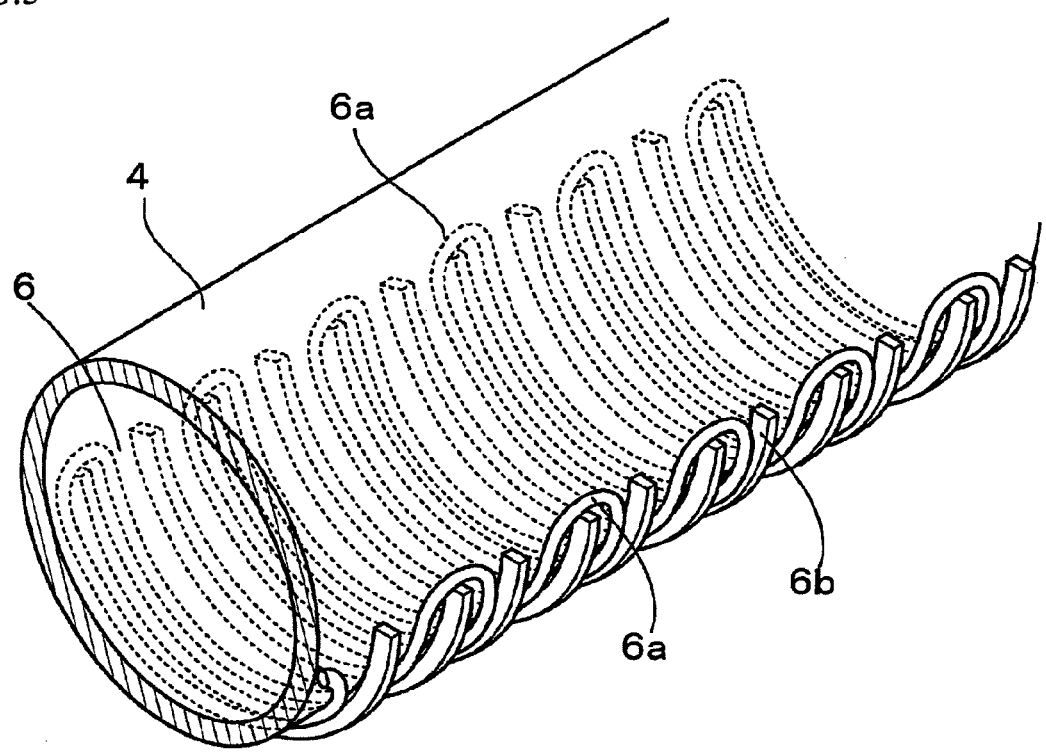
FIG. 3 is a partially cutaway perspective view illustrating the drying unit of the fermentation device.

Further, as illustrated in FIGS. 2 and 3, a hot-water pipe 6a is arranged in a meandering manner on a lower outer peripheral wall of the drying unit 6 by means of a shuttering board 6b, and hot water is allowed to flow through the hot-water pipe 6a to be used in the drying treatment.

Meanwhile, although not specifically illustrated, a fixed stirring blade is provided in a longitudinal axis line direction inside the cylindrical kiln 4 and a rotational device, which rotates the cylindrical kiln 4 itself around a longitudinal central axis thereof, is provided outside the cylindrical kiln 4, and it is configured to promote the fermentation treatment and the drying treatment by stirring and breaking the wet organic waste and the fermented material into pieces by rotation of the cylindrical kiln 4 and the stirring blade.

Although the cylindrical kiln 4 is arranged with downward inclination from a front end side toward a rear end side such that the wet organic waste and the fermented material gradually move from the front end side toward the rear end side in the standard kiln-type fermentation device, the present invention is not limited to this, and horizontal arrangement of the cylindrical kiln 4 and gradual movement of the wet organic waste and the fermented material from the front end side toward the rear end side by means of a helical stirring blade, for example, are also realized voluntarily according to implementation.

Figure 4:
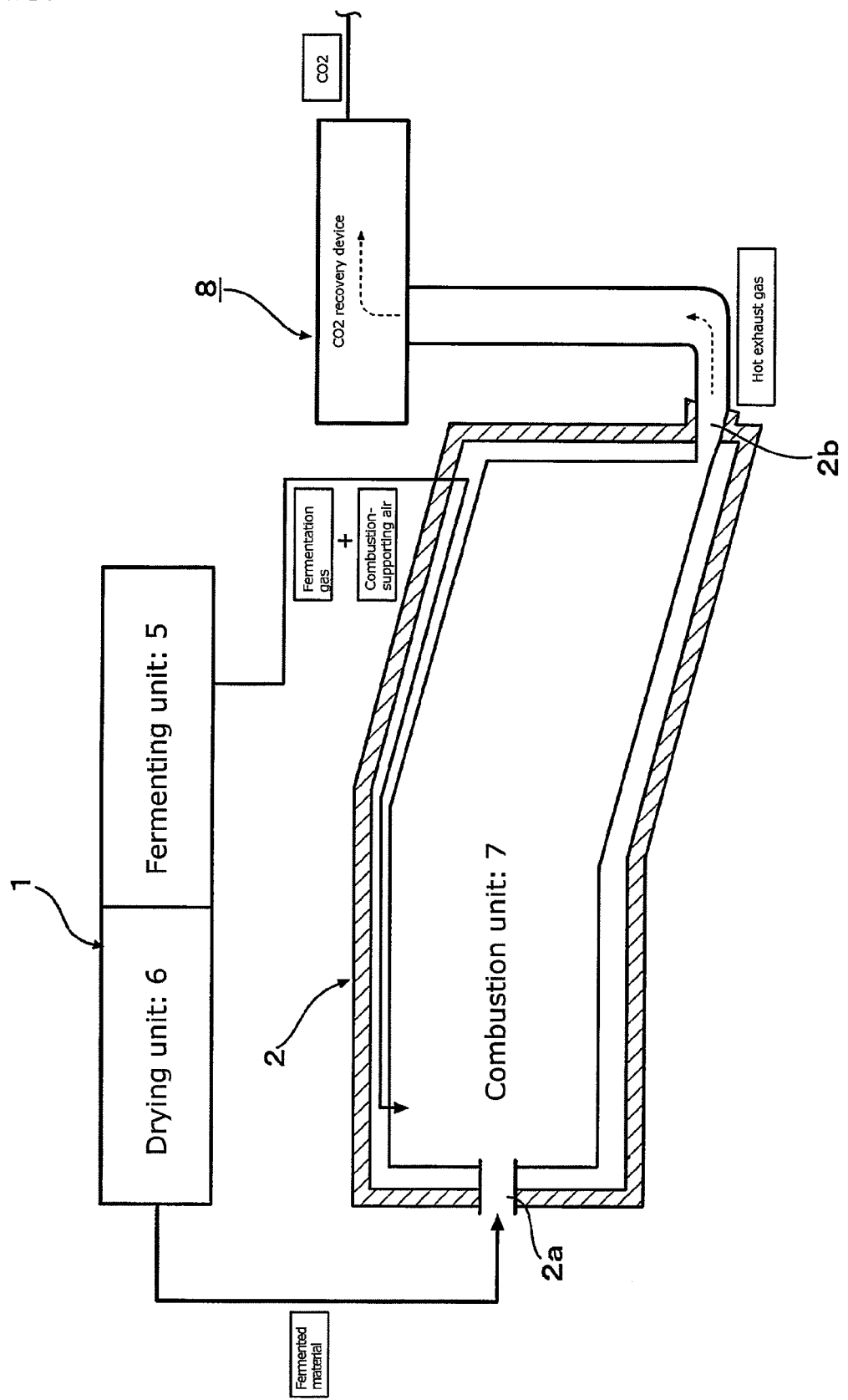
FIG. 4 is an illustrative diagram schematically illustrating an inner structure of a combustion furnace and a $CO_2$ recovery device according to the first embodiment of the present invention.

Next, the combustion furnace 2 is described in detail; as illustrated in FIG. 4, the combustion furnace 2 is provided with a supply port 2a of the fermented material obtained from the fermentation device 1 on a front end thereof, a combustion unit 7, which performs the combustion treatment of the fermented material, on the inside thereof subsequent to the supply port 2a, and a discharge port 2b through which the hot exhaust gas produced by the combustion treatment is discharged on a rear end of the combustion unit 7, and is configured such that the hot exhaust gas discharged from the discharge port 2b is supplied to a $CO_2$ recovery device 8.

In actual use, the wet organic waste such as a food residue and sewage sludge is put into the fermenting unit 5 through the input port 4a provided on the front end of the cylindrical kiln 4 of the fermentation device 1 together with a moistening material (not illustrated) and the microbial fermentation treatment of the wet organic waste is performed by the aerobic bacteria.

Then, the fermented material obtained by the microbial fermentation treatment in the fermenting unit 5 gradually moves toward the drying unit 6, and after the drying treatment is performed in the drying unit 6, this is taken out through the output port 4b to be supplied to the combustion furnace 2.

Meanwhile, although the fermented material obtained from the fermentation device 1 is used as fuel in the present invention, a part of the fermented material, which is taken out through the output port 4b of the cylindrical kiln 4, is voluntarily used as compost to grow the plant without being supplied to the combustion furnace 2 according to the implementation.

On the other hand, the fermentation gas including heat is also produced by the microbial fermentation treatment in the fermenting unit 5, and the fermentation gas is recovered from the fermenting unit 5 to be supplied to the combustion furnace 2.

Meanwhile, in the present invention, especially, the fermenting unit 5, which performs the microbial fermentation treatment, is provided on the front half side of the inside of the cylindrical kiln 4 and the drying unit 6, which performs the drying treatment of the fermented material subjected to the fermentation treatment in the fermenting unit 5, is provided on the rear half side of the inside thereof, and the fermentation gas is recovered from the fermenting unit 5 and the fermentation gas including the heat is efficiently recovered.

In addition to this, the combustion-supporting air is actively supplied to the drying unit 6 through the vent 4c of the fermentation device 1, the combustion-supporting air is allowed to flow to the fermenting unit 5 while being heated in the drying unit 6 to promote the fermentation treatment, and the combustion-supporting air is recovered together with the fermentation gas to be supplied to the combustion furnace 2 as the combustion-supporting gas, thereby promoting the combustion treatment of the fermented material in the combustion furnace 2. Meanwhile, at that time, the water vapor produced by the drying treatment in the drying unit 6 is recovered together to be supplied to the combustion furnace 2.

The fermented material supplied to the combustion furnace 2 is put in through the supply port 2a and is subjected to the combustion treatment in the combustion unit 7 while combustion thereof is promoted by the combustion-supporting air, the hot exhaust gas is produced by the combustion treatment, and the hot exhaust gas is supplied to the $CO_2$ recovery device 8 through the discharge port 2b.

The fermentation gas supplied together with the combustion-supporting air and the water vapor at the time of the drying treatment are also subjected to the combustion treatment or heating treatment in the combustion unit 7. Meanwhile, the fermentation gas and water vapor are included in the hot exhaust gas to be supplied to the $CO_2$ recovery device 8 through the discharge port 2b after the combustion treatment or the heating treatment.

Then, by recovering $CO_2$ in the hot exhaust gas by the $CO_2$ recovery device 8 and supplying the same to the plant growth facility 3, the photonic synthesis of the plant is promoted and $CO_2$ is immobilized, and it becomes possible to prevent $CO_2$ from being released again into the atmosphere.

Second Embodiment

The treatment system of the wet organic waste according to a second embodiment is basically configured to perform the microbial fermentation treatment of the wet organic waste by the aerobic bacteria in the fermentation device 1, perform the combustion treatment of the fermented material obtained from the fermentation device 1 in the combustion furnace 2, and at the same time, supply the fermentation gas produced by the microbial fermentation treatment in the fermentation device 1 to the combustion furnace 2 together with the combustion-supporting air as the combustion-supporting gas, and supply $CO_2$ in the hot exhaust gas produced by the combustion treatment in the combustion furnace 2 to the plant growth facility 3 to promote the photonic synthesis of the plant as in the first embodiment.

Figure 5:
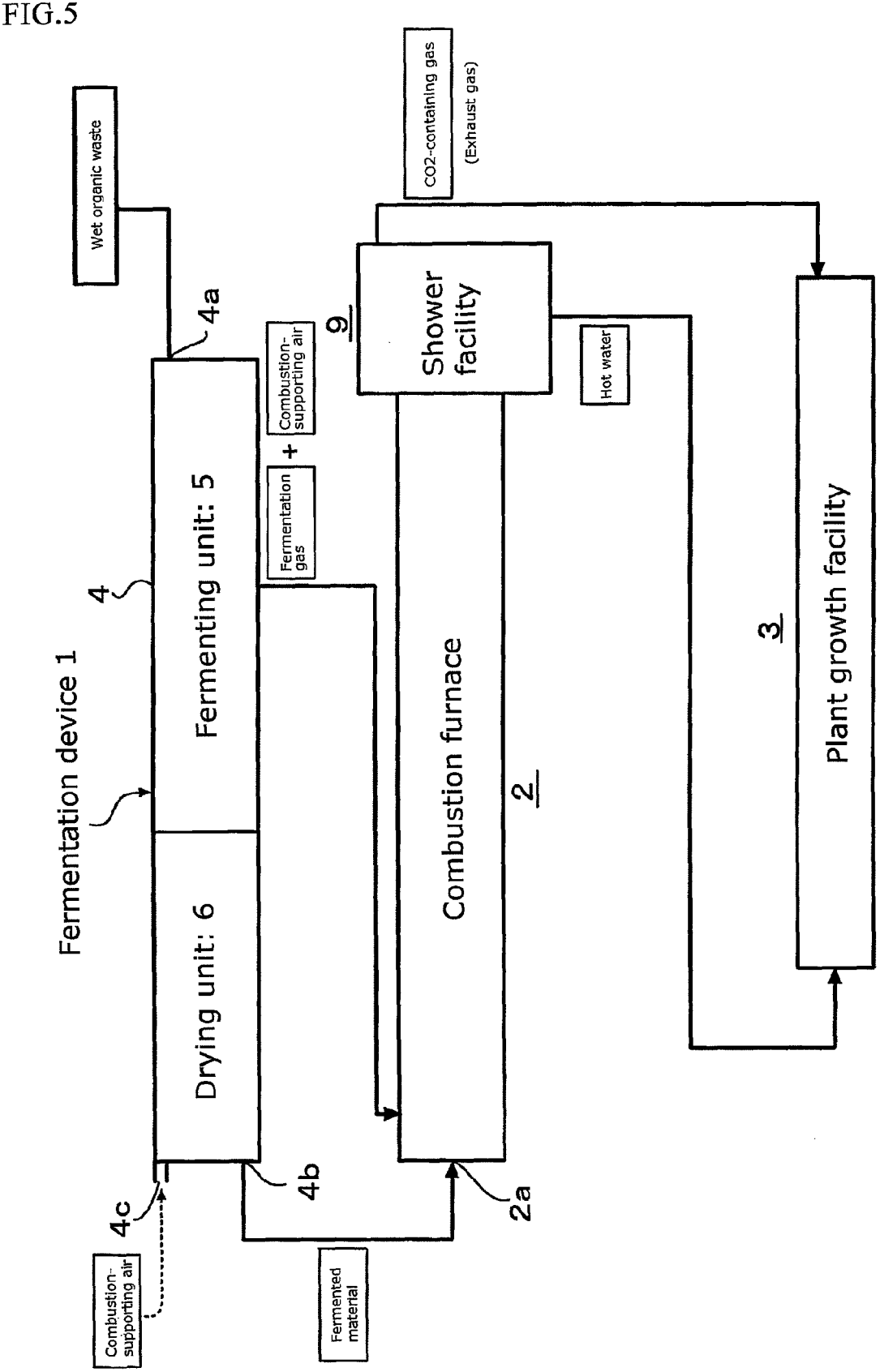
FIG. 5 is a flowchart schematically illustrating the treatment system of the wet organic waste according to a second embodiment of the present invention.

The second embodiment is characterized by including a shower facility 9, which performs wash treatment of the hot exhaust gas produced by the combustion treatment in the combustion furnace 2 by a shower, and by supplying the hot water obtained by contact between shower water and the hot exhaust gas to the plant growth facility 3 to use for heating the facility as illustrated in FIG. 5.

Figure 6:
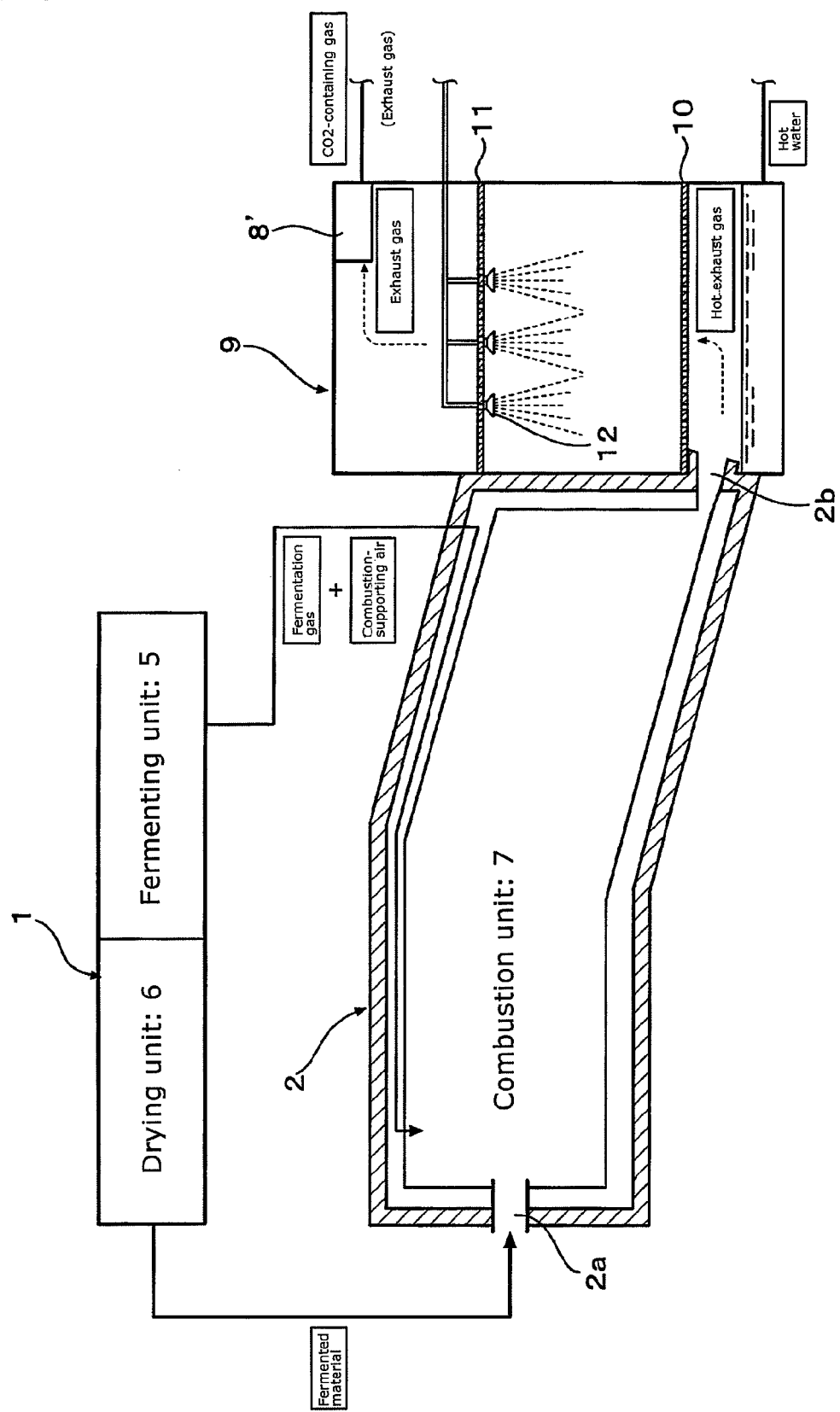
FIG. 6 is an illustrative diagram schematically illustrating an inner structure of the combustion furnace and a shower facility according to the second embodiment of the present invention.

The shower facility 9 is described in detail; as illustrated in FIG. 6, the shower facility 9 is connected to the discharge port 2b of the combustion furnace 2 on a lower end side thereof and is provided with a first porous plate 10 provided on an inner lower portion thereof and a second porous plate 11 provided at an interval above the first porous plate 10, the first and second porous plates 10 and 11 dividing the inner portion thereof into three parts in a vertical direction, and a plurality of showers 12, which spray water on a lower surface of the second porous plate 11.

It is configured such that the hot exhaust gas produced in the combustion furnace 2 is taken in through the discharge port 2b, the wash treatment of the hot exhaust gas, which passes through the first porous plate 10 from below upward, is performed by the shower 12, and thereafter, the exhaust gas of which temperature is decreased after the wash treatment passes through the second porous plate 11 from below upward.

Further, it is configured such that, since the hot water obtained by the contact between the shower water and hot exhaust gas is accumulated on the lower end side of the shower facility 9, the hot water is recovered from the lower end side, and on the other hand, since the exhaust gas of which temperature is decreased after the wash treatment finally ascends toward an upper end side of the shower facility 9, the exhaust gas is discharged from the upper end side by means of a blower 8' to be recovered.

In the actual use, although the treatment in the fermentation device 1 and that in the combustion furnace 2 are the same as those of the first embodiment, in the second embodiment, the hot exhaust gas produced by the combustion treatment in the combustion unit 7 of the combustion furnace 2 is supplied to the shower facility 9 through the discharge port 2b.

Then, the hot exhaust gas supplied to the shower facility 9 is taken in from the lower end side of the shower facility 9 to which the discharge port 2b is connected to ascend toward the upper end side thereof; first, this passes through the first porous plate 10 from below upward to remove combustion ash and the like, and then this is sprayed with the water by the shower 12 to be subjected to the wash treatment.

At that time, since heat exchange is also performed by the contact between the shower water and the hot exhaust gas, the shower water is heated, and at the same time, the water vapor in the hot exhaust gas is liquidized and the hot water is produced, so that it becomes possible to use heat energy of the hot exhaust gas and the water vapor in the hot exhaust gas without waste.

Then, the hot water passes through the first porous plate 10 from above downward to be accumulated on the lower end side of the shower facility 9, so that the hot water is recovered from the lower end side.

On the other hand, the hot exhaust gas subjected to the wash treatment by the shower 12 becomes the exhaust gas of which temperature is decreased and further ascends to pass through the second porous plate 11 from below upward to remove the combustion ash and the like, which is not completely removed by the first porous plate 10 and the shower water, and ascends toward the upper end side of the shower facility 9, so that the exhaust gas, that is to say, $CO_2$-containing gas is discharged from the upper end side thereof by means of the blower 8' to be recovered.

Finally, while the $CO_2$-containing gas (exhaust gas) recovered in the shower facility 9 is supplied to the plant growth facility 3 to promote the photonic synthesis of the plant, the hot water recovered in the shower facility 9 is supplied to the plant growth facility 3 to be used for heating the facility, so that it becomes possible to immobilize $CO_2$ and to stably grow the plant.

Meanwhile, in the present invention, if the hot water is recovered again to be supplied to the hot-water pipe 6a in the drying unit 6 of the fermentation device 1 after this is used for heating the plant growth facility 3, a synergic effect of the system is further improved. Further, direct supply of a part or all of the hot water to the hot-water pipe 6a in the drying unit 6 of the fermentation device 1 after recovery of the hot water in the shower facility 9 is not excluded.

Third Embodiment

Figure 7:
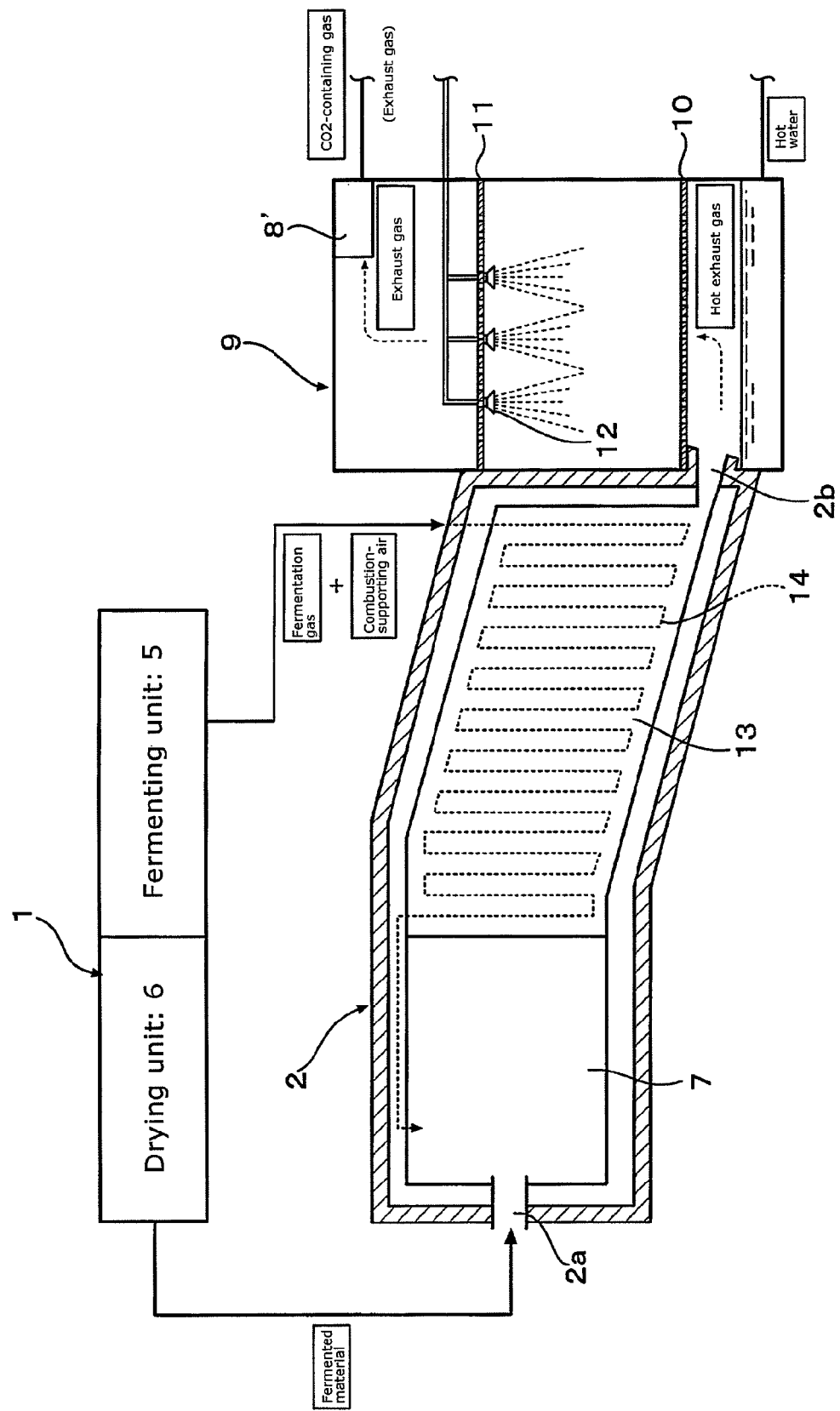
FIG. 7 is an illustrative diagram schematically illustrating the inner structure of the combustion furnace and the shower facility according to a third embodiment of the present invention.

Although the configuration of the treatment system of the wet organic waste according to a third embodiment is basically similar to that of the second embodiment, the third embodiment is characterized in that the combustion furnace 2 is provided with a heat exchanger 13, which performs the heat exchange between the fermentation gas and the combustion-supporting air recovered from the fermenting unit 5 of the fermentation device 1 and the hot exhaust gas produced by the combustion treatment in the combustion furnace 2 as illustrated in FIG. 7 and that the fermentation gas and the combustion-supporting air heated by the heat exchanger 13 are supplied to the combustion furnace 2 as the combustion-supporting gas.

The combustion furnace 2 is described in detail; the combustion furnace 2 is provided with the supply port 2a of the fermented material obtained from the fermentation device 1 on the front end thereof, the combustion unit 7 and the heat exchanger 13 in a continuous manner on the inside thereof subsequent to the supply port 2a, and the discharge port 2b on an end of the heat exchanger 13, and the heat exchanger 13 includes a supply pipe 14, which supplies the fermentation gas and the combustion-supporting air to the combustion unit 7, arranged on the inside thereof in a meandering manner and is configured such that, when the fermentation gas and combustion-supporting air pass through the supply pipe 14, the heat exchange between them and the hot exhaust gas is performed.

In the actual use, although a basic flow is the same as that of the second embodiment, especially, in the third embodiment, when the fermentation gas and the combustion-supporting air recovered from the fermenting unit 5 of the fermentation device 1 are supplied to the combustion furnace 2, the fermentation gas and the combustion-supporting air pass through the supply pipe 14 arranged in the heat exchanger 13 of the combustion furnace 2 and the heat exchange between them and the hot exhaust gas produced by the combustion treatment in the combustion unit 7 is performed.

Therefore, the fermentation gas and combustion-supporting air are supplied to the combustion unit 7 of the combustion furnace 2 after being heated by the heat exchange, and it becomes possible to effectively perform the combustion treatment or the heating treatment of the fermentation gas and it becomes possible that the combustion-supporting air certainly promotes the combustion treatment.

INDUSTRIAL APPLICABILITY

The treatment system of the wet organic waste according to the present invention is capable of performing the microbial fermentation treatment of the wet organic waste and the combustion treatment of the fermented material obtained thereby, and at the same time, performing the combustion treatment or the heating treatment of the fermentation gas also obtained by the microbial fermentation treatment in the combustion furnace, and immobilizing $CO_2$ in the hot exhaust gas to contribute to reduction in $CO_2$, so that this is extremely advantageously used in the treatment of the wet organic waste such as the food residue and the sewage sludge of which treatment amount is increasing.

REFERENCE SIGNS LIST 1 fermentation device
2 combustion furnace
2a supply port
2b discharge port
3 plant growth facility
4 cylindrical kiln
4a input port
4b output port
4c vent
5 fermenting unit
6 drying unit
7 combustion unit
8 $CO_2$ recovery device
8' blower
9 shower facility
10 first porous plate
11 second porous plate
12 shower
13 heat exchanger
14 supply pipe

The invention claimed is:
1. A treatment system of a wet organic waste, comprising a fermentation device and a combustion furnace,
wherein microbial fermentation treatment of the wet organic waste is performed in the fermentation device, combustion treatment of a fermented material obtained from the fermentation device is performed in the combustion furnace, and at the same time, fermentation gas produced by the microbial fermentation treatment in the fermentation device is supplied to the combustion furnace, and $CO_2$ in hot exhaust gas produced by the combustion treatment in the combustion furnace is recovered to be immobilized,
wherein the fermentation device includes a fermenting unit, which performs the microbial fermentation treatment, on a front half side of the inside of a cylindrical kiln, and a drying unit, which performs drying treatment of the fermented material subjected to the microbial fermentation treatment in the fermenting unit, on a rear half side of the inside of the cylindrical kiln, wherein the fermentation device further includes a vent through which the combustion-supporting air is delivered, on a rear end of the cylindrical kiln, and wherein the combustion-supporting air is actively supplied to the drying unit through the vent, the combustion-supporting air is allowed to flow to the fermenting unit while being heated in the drying unit to promote the fermentation treatment, and the combustion-supporting air is recovered from the fermenting unit, together with the fermentation gas, to be supplied to the combustion furnace as the combustion-supporting gas, thereby promoting the combustion treatment of the fermented material in the combustion furnace.

2. The treatment system of a wet organic waste according to claim 1, wherein $CO_2$ in the hot exhaust gas is supplied to a plant growth facility to promote photonic synthesis of a plant, thereby immobilizing $CO_2$.

3. A treatment system of a wet organic waste according to claim 1, wherein wherein the hot exhaust gas is subjected to wash treatment by a shower, and hot water obtained by contact between the shower water and the hot exhaust gas is supplied to a plant growth facility to be used for heating the facility.

4. The treatment system of a wet organic waste according to claim 1, wherein heat exchange is performed between the fermentation gas produced by the microbial fermentation treatment in the fermentation device and the hot exhaust gas produced by the combustion treatment in the combustion furnace, and the fermentation gas heated by the heat exchange is supplied to the combustion furnace.

5. The treatment system of a wet organic waste according to claim 2, wherein heat exchange is performed between the fermentation gas produced by the microbial fermentation treatment in the fermentation device and the hot exhaust gas produced by the combustion treatment in the combustion furnace, and the fermentation gas heated by the heat exchange is supplied to the combustion furnace.

6. The treatment system of a wet organic waste according to claim 3, wherein heat exchange is performed between the fermentation gas produced by the microbial fermentation treatment in the fermentation device and the hot exhaust gas produced by the combustion treatment in the combustion furnace, and the fermentation gas heated by the heat exchange is supplied to the combustion furnace.

* * * * *